(12) United States Patent
Boyer

(10) Patent No.: US 9,700,218 B2
(45) Date of Patent: Jul. 11, 2017

(54) SYSTEMS AND METHODS FOR REDUCING NUISANCE ALARMS IN MEDICAL DEVICES

(71) Applicant: COVIDIEN LP, Mansfield, MA (US)

(72) Inventor: Robert T. Boyer, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/858,827

(22) Filed: Sep. 18, 2015

(65) Prior Publication Data

US 2016/0093205 A1 Mar. 31, 2016

Related U.S. Application Data

(60) Provisional application No. 62/056,981, filed on Sep. 29, 2014.

(51) Int. Cl.
G08B 21/00 (2006.01)
A61B 5/024 (2006.01)
A61B 5/00 (2006.01)

(52) U.S. Cl.
CPC .......... *A61B 5/02416* (2013.01); *A61B 5/746* (2013.01)

(58) Field of Classification Search
CPC .......................... A61B 5/02416; A61B 5/746
USPC ...................................................... 340/506
See application file for complete search history.

(56) References Cited

U.S. PATENT DOCUMENTS

| | | | |
|---|---|---|---|
| 5,864,736 A | 1/1999 | Shimada et al. | |
| 5,920,263 A | 7/1999 | Huttenhoff et al. | |
| 6,754,516 B2 | 6/2004 | Mannheimer | |
| 7,161,484 B2 | 1/2007 | Tsoukalis | |
| 7,353,238 B1 | 4/2008 | Gliklich | |
| 7,398,115 B2 | 7/2008 | Lynn | |
| 8,430,817 B1 | 4/2013 | Al-Ali et al. | |
| 8,608,656 B2 | 12/2013 | Greenwald et al. | |
| 8,979,753 B2 | 3/2015 | Corsetti et al. | |
| 2007/0032714 A1* | 2/2007 | Mannheimer | A61B 5/02455 600/323 |
| 2007/0093721 A1 | 4/2007 | Lynn et al. | |
| 2007/0208259 A1 | 9/2007 | Mannheimer | |
| 2007/0225575 A1 | 9/2007 | Kilborn et al. | |
| 2007/0225580 A1 | 9/2007 | Wang | |
| 2008/0214906 A1 | 9/2008 | Wang et al. | |
| 2008/0281168 A1 | 11/2008 | Gibson et al. | |
| 2008/0287756 A1 | 11/2008 | Lynn | |
| 2009/0149719 A1 | 6/2009 | Wariar et al. | |
| 2010/0298656 A1* | 11/2010 | McCombie | A61B 5/02028 600/301 |

(Continued)

OTHER PUBLICATIONS

Inokuchi R, Sato H, Nanjo Y, et al. The proportion of clinically relevant alarms decreases as patient clinical severity decreases in intensive care units: a pilot study. BMJ Open 2013;3: e003354. doi:10.1136/bmjopen-2013-003354.

*Primary Examiner* — Mark Rushing
(74) *Attorney, Agent, or Firm* — Fletcher Yoder, P.C.

(57) ABSTRACT

A method for storing data relating to generated alarms includes receiving a physiological signal or a physiological parameter value. The method also includes generating an alarm in response to a determination that the physiological signal or physiological parameter value meets an alarm condition. Additionally, the method includes receiving a relevance indicator indicating a relevance of the generated alarm and storing the relevance indicator and the alarm condition.

20 Claims, 7 Drawing Sheets

(56) References Cited

U.S. PATENT DOCUMENTS

| | | | |
|---|---|---|---|
| 2011/0066007 A1* | 3/2011 | Banet | A61B 5/0402 600/301 |
| 2014/0043164 A1 | 2/2014 | Eschelman et al. | |
| 2015/0137968 A1* | 5/2015 | Rusin | G08B 25/001 340/506 |
| 2015/0186608 A1* | 7/2015 | Fuller | G06F 19/3406 705/2 |
| 2015/0190100 A1* | 7/2015 | Fox | A61B 5/746 340/539.12 |

* cited by examiner

SYSTEMS AND METHODS FOR REDUCING NUISANCE ALARMS IN MEDICAL DEVICES

CROSS-REFERENCE TO RELATED APPLICATION

This application claims priority to U.S. Provisional Application No. 62/056,981, filed Sep. 29, 2014, the disclosure of which is hereby incorporated by reference in its entirety for all purposes.

BACKGROUND

The present disclosure relates generally to alarm management in medical devices, and in particular to a system and method for improving the clinical significance of alarms.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Alarm management in medical facilities is drawing attention as an important aspect of medical care. Alarms are generated by many types of medical devices, including monitoring devices (for example, capnography monitors, pulse oximeters, heart rate monitors, and others) and therapeutic devices (for example, ventilators, infusion pumps, and others). These medical devices generate alarms based on patient conditions, device status, and stored alarm algorithms. The purpose of these alarms is to alert caregivers when the patient's condition may be deteriorating, in case medical intervention is needed, or when the medical device may not be operating properly.

Nuisance alarms—alarms that do not correspond to a clinically significant event—are becoming an increasingly serious concern in many medical facilities. Nuisance alarms may be caused by false readings by the medical equipment, or by conservative or sub-optimal alarm algorithms that trigger when the patient's physiologic condition has not changed in a significant way. Nuisance alarms detract from the quality of medical care by disrupting patients, distracting clinicians, and contributing to alarm fatigue. When a caregiver suffers from alarm fatigue due to exposure to a high number of nuisance alarms, the risk increases that the caregiver becomes de-sensitized to alarms, thereby inadvertently ignoring or missing a true alarm event.

SUMMARY

In a first embodiment, a method is provided that includes receiving a physiological signal or a physiological parameter value. The method also includes generating an alarm in response to a determination that the physiological signal or physiological parameter value meets an alarm condition. Additionally, the method includes receiving a relevance indicator indicating a relevance of the generated alarm and storing the relevance indicator and the alarm condition.

In a second embodiment, a method is provided that includes receiving data associated with a plurality of generated alarms. Each of the plurality of generated alarms is generated in response to a determination that a respective physiological parameter of a patient meets a respective alarm condition. The method also includes receiving a plurality of relevance indicators indicating a relevance of each of the plurality of generated alarms. Additionally, the method includes analyzing the data associated with the plurality of generated alarms and the plurality of relevance indicators. Further, the method includes modifying at least one alarm condition of the alarm conditions based on the analysis.

In a third embodiment, a medical device is provided that includes a signal input configured to receive a physiologic parameter value. The medical device also includes a processor configured to activate an alarm in response to a determination that the physiologic parameter value meets an alarm condition. Additionally, the medical device includes a user input configured to generate a relevance indicator indicating a relevance of the alarm. Further, the medical device includes a memory configured to store the relevance indicator and the alarm condition.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to alarm management in medical devices, and in particular to a system and method for improving the clinical significance of alarms and reducing the occurrence of alarms that do not correspond to a clinically significant event. Alarms that do not correspond to a clinically significant event may be referred to as nuisance alarms or false alarms. In an embodiment, a medical device, such as a monitoring device or a therapeutic device, includes a user input that receives an indicator of the relevance or significance of a generated alarm. When an alarm is generated, the caregiver who responds to the alarm can provide feedback by activating the user input to indicate the relevance of the alarm. For example, the user input may press a button or select an icon to generate an indicator that the triggered alarm corresponded to a clinically significant or relevant event, or that the triggered alarm did not correspond to a clinically significant or relevant event. In another example, the user input may include a rating scale that receives a numerical value from the user regarding the relevance of the alarm on a numerical scale. Thus, the relevance indicator may be a binary indication (relevant or not relevant), a numerical value (indicating a relevance value), a category, or other inputs as described below. The medical device receives this feedback and stores the relevance indicator along with information about the alarm event, such as the alarm condition, the medical device status, and the patient's physiological status. Together, this relevance event data is then further analyzed to identify alarm protocols that have low relevance, and to modify those alarm protocols or to create new alarm protocols that decrease the prevalence of nuisance alarms.

Figure 1:
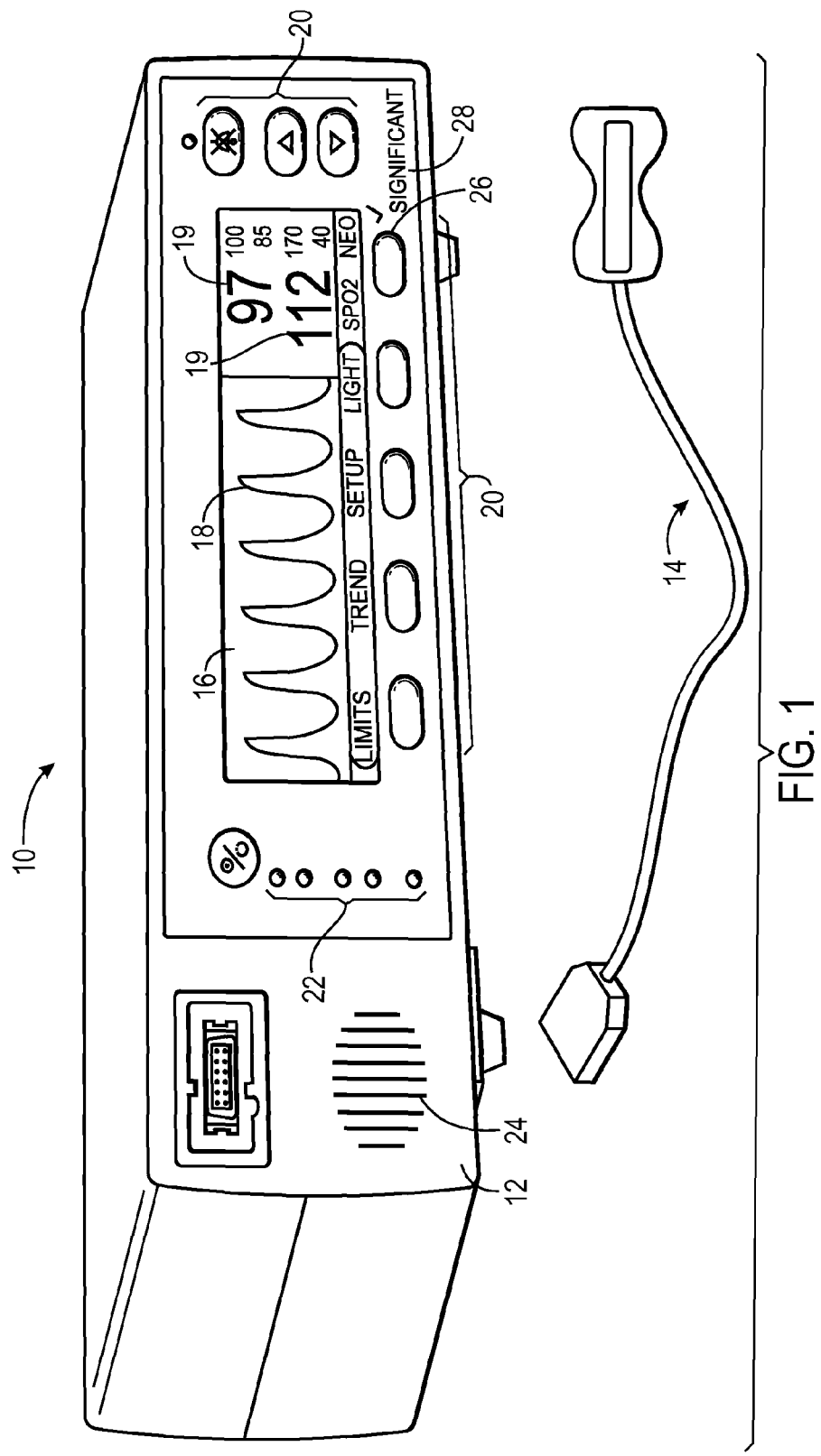
FIG. 1 is a perspective view of a medical monitor with an alarm relevance input, in accordance with an embodiment.

With the foregoing in mind, FIG. 1 illustrates a medical device 10 including an alarm relevance input in accordance with an embodiment. In the illustrated example, the medical device 10 is a medical monitor 12. Examples of such monitors include pulse oximeters, regional oximeters, electroencephalography (EEG) monitors, capnography monitors, depth of anesthesia monitors, and monitors that measure blood pressure, temperature, glucose, tissue water fraction, and other parameters. The monitor 12 is coupled to a sensor 14 for monitoring one or more physiological parameters of a patient. For example, the monitor 12 may receive a physiologic signal from the sensor 14, and the monitor 12 may be configured to generate a physiologic waveform and/or calculate or measure one or more physiological parameters based on the physiologic signal.

In the illustrated example, the monitor 12 is a pulse oximetry monitor and the sensor 14 is a pulse oximetry sensor. For example, the sensor 14 may include at least two emitters, which may emit light at two different wavelengths, and at least one detector for detecting photoplethysmography (PPG) signals from the patient tissue. The monitor 12 may include a processor configured to execute code (e.g., stored in a memory of the monitor 12 or received from another device) for filtering and processing the signals from the sensor 14 to calculate physiologic parameters, such as oxygen saturation ($SpO_2$) and pulse rate. In other embodiments, the monitor 12 may calculate or measure a different parameter or combination of parameters. For example, the monitor 12 may be a regional oximeter. In such an embodiment, the sensor 14 includes at least two emitters and at least two detectors for detecting PPG signals at different depths, and the monitor 12 processes the PPG signals to calculate regional oxygen saturation ($rSO_2$). In another embodiment, the monitor 12 may be a capnography monitor. In such an embodiment, the sensor 14 may include a detector that detects a photonic signal that has passed through a gas sample, and the monitor 12 may calculate the presence and concentration of carbon dioxide in the photonic signal. It should be appreciated that these are merely provided as examples, and other types of medical monitors may be used, such as the medical monitors noted above and multi-parameter monitors.

As illustrated in FIG. 1, the monitor 12 includes a display 16 displaying a physiological waveform 18, such as a PPG waveform, a capnogram, or any other suitable physiological waveforms, and one or more calculated physiologic parameters 19, such as oxygen saturation, heart or pulse rate, tissue perfusion, EEG, temperature, respiration rate, end tidal carbon dioxide ($etCO_2$), blood pressure, glucose, tissue water fraction, hemoglobin, or any other suitable physiologic parameters. The display 16 may also display information related to alarms, monitor settings, and/or signal quality. In certain embodiments, the display 16 may be a touch screen display.

The monitor 12 also includes various control inputs 20 for receiving user inputs. The control inputs 20 may be fixed function keys, programmable function keys, mechanical buttons, soft keys (corresponding to icons on the display 16), knobs, switches, or other mechanisms. Though the illustrated control inputs 20 are physical buttons, in other embodiments, the control inputs 20 may be selectable icons on a touch screen display 16 or other virtual controls. As explained in more detail below, in some embodiments, at least one user input 20 may be programmed to generate an indicator regarding the relevance of a triggered alarm.

An alarm is generated by a medical device (such as the monitor 12 or a therapeutic device, such as a ventilator) when an alarm condition or protocol is met. Alarm conditions include several types, such as physiologic alarm conditions, patient event alarm conditions, and device alarm conditions. Physiologic alarm conditions trigger an alarm when a measured or calculated physiologic parameter satisfies an alarm condition, such as when the parameter value crosses a threshold, deviates from a specified range, matches a stored pattern, deviates from a threshold for a specified time and/or extent (e.g., exceeding a limit on a value of an integral taken between the parameter value and a threshold), or meets other conditions that indicate a clinically significant event. Patient event alarm conditions trigger an alarm when a patient takes certain actions, such as attempting to speak, standing, or moving in a way that interferes with the physiologic signal (motion interference or motion artifact). Device alarm conditions trigger an alarm when the medical device identifies a problematic status, such as power loss, low battery, sensor disconnect from the monitor or the patient, electromagnetic interference, line or flow blockage, equipment failure, and other conditions. Further, alarm conditions may be based on a combination of different alarm conditions, such as two physiologic parameters each violating a respective limit, a combined alarm index violating a limit, or specified combinations of monitor and sensor status events. Referring to FIG. 1, when an alarm is generated by the monitor 12, textual or graphical alarm information may be displayed on the display 16, visible warning lights such as indicator lights 22 may be illuminated, and an audible warning may be sounded via speaker 24.

In the embodiment illustrated in FIG. 1, the monitor 12 includes a control input 26 configured to receive a user input regarding alarm significant or relevance. As illustrated, the control input 26 may be a mechanical button that, when pressed, generates an indicator that the triggered alarm was associated with a clinically significant event. However, as noted above, in other embodiments, the control input 26 may be a touch-sensitive icon on a touch screen display 16, a soft key, knob, or other mechanism. The monitor 12 may include a label 28 associated with the control input 26 to provide information to the user regarding the function of the control input 26. For example, the label 28 may include text that states "Significant." Other text such as "Useful" or "Relevant", or graphical icons such as a check mark may be used. Further, in other embodiments, the control input 26 may generate an indicator that the triggered alarm was not associated with a clinically significant event. Accordingly, the label 28 may include corresponding text such as "Not Significant" or "Nuisance" or may include a suitable graphic icon such as an "X" mark.

Figure 2:
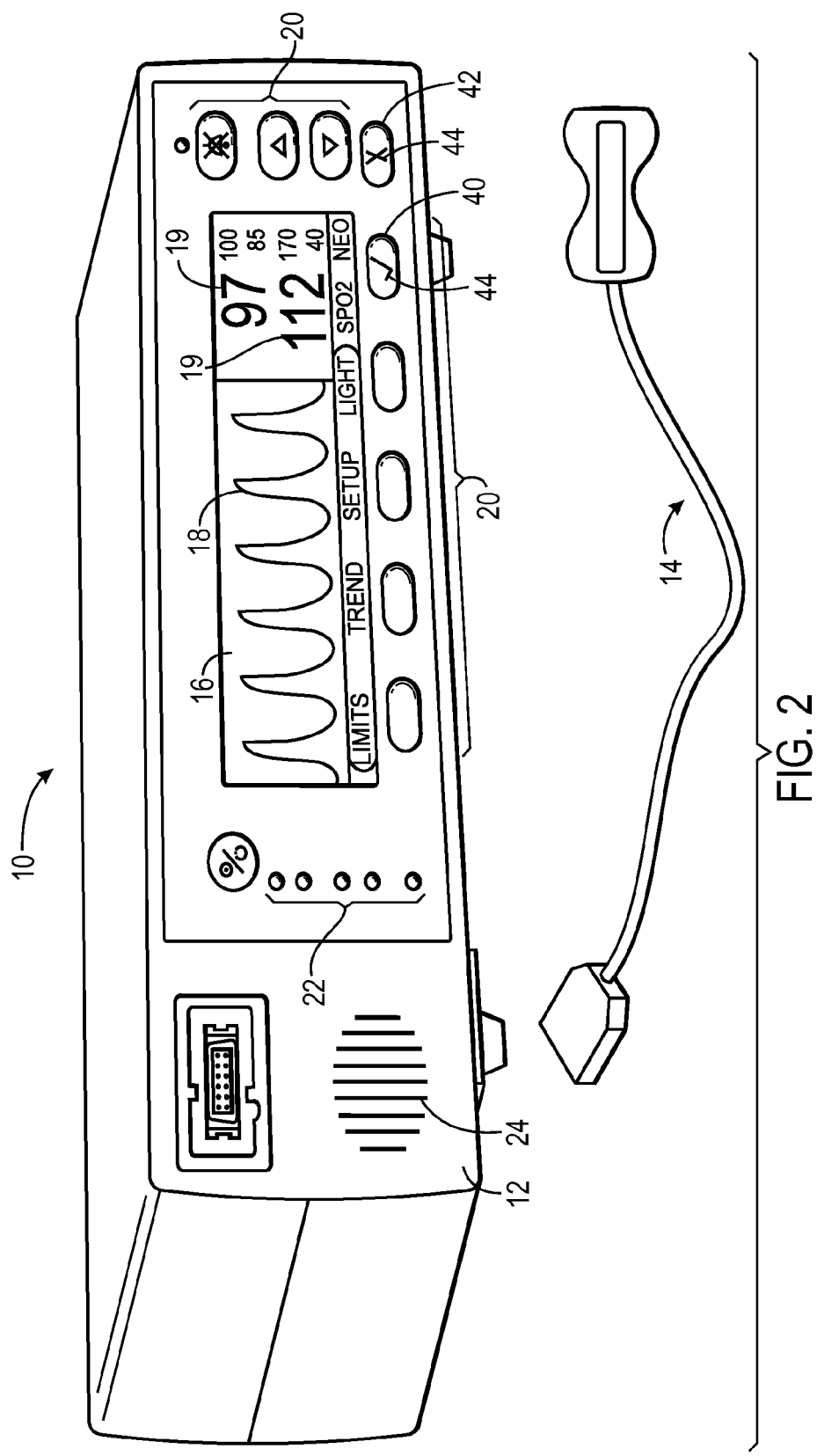
FIG. 2 is a perspective view of a medical monitor with two alarm relevance inputs, in accordance with an embodiment.

In the embodiment of FIG. 1, a single relevance input 26 is included, allowing the user to provide a single type of response (e.g., relevant or not relevant) or no response at all. In other embodiments, the control inputs 20 of the monitor 12 may include two relevance inputs 40 and 42, as illustrated in FIG. 2. When pressed, the first relevance input 40 generates an indicator that the triggered alarm was associated with a clinically significant event, and, when pressed, the second relevance input 42 generates an indicator that the alarm was not associated with a clinically significant event. By providing the two relevance inputs 40 and 42, the monitor 12 may capture three possible alarm relevance states (i.e., no relevance provided, significant alarm, and insignificant alarm). The monitor 12 may also include labels 44, such as those described above with respect to FIG. 1, to assist the user in identifying the first relevance input 40 and the second relevance input 42.

Figure 3:
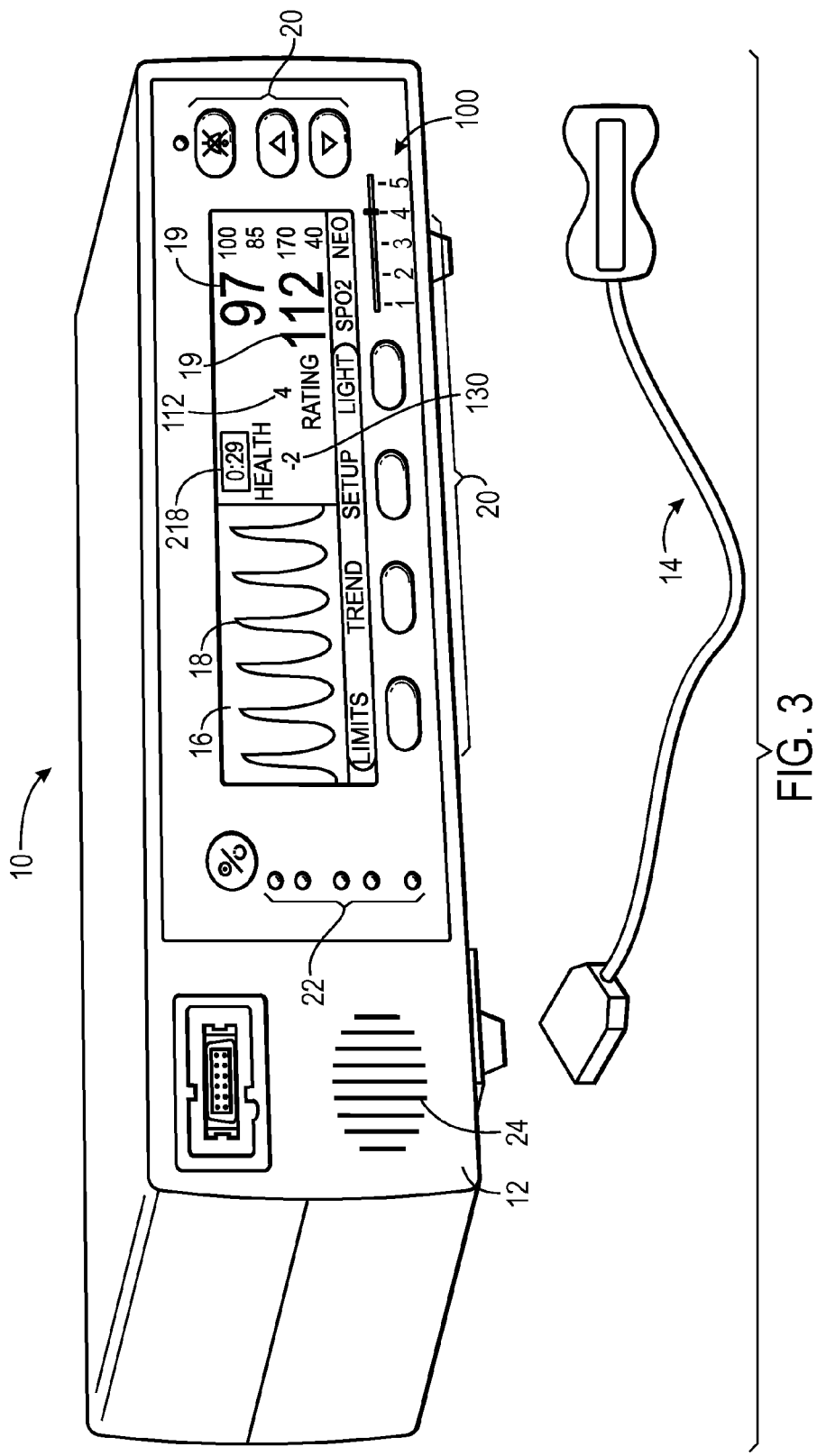
FIG. 3 is a perspective view of a medical monitor with an alarm relevance input including a rating input, in accordance with an embodiment.

In some embodiments, it may be desirable to rate the clinical significance of a triggered alarm to help quantify the significance of the alarm with more than binary feedback. For example, as illustrated in FIG. 3, the monitor 12 may include a rating scale 100, which the user may use to select a rating for a triggered alarm. For example, the rating scale 100 may display a range of possible significance, relevance, or helpfulness ratings. In some embodiments, the rating scale 100 may be a Likert-type scale that includes positive significance ratings, neutral significance ratings, and negative significance ratings. For example, the rating scale 100 may display a range of possible significance ratings such as strongly disagree, disagree, neither agree nor disagree, agree, and strongly agree. In another embodiment, the rating scale 100 may display a range of possible significance ratings such as very significant, significant, neither significant nor insignificant, insignificant, and very insignificant. It should be appreciated that in other embodiments, other words may be used in place of significant, such as relevant, helpful, or good, and other words may be used in place of insignificant, such as not relevant, not helpful, nuisance, or bad. In other embodiments, the rating scale 100 may display a numeric scale, such as a scale from 1 to 5 (e.g., 1, 2, 3, 4, and 5) or a scale from one 1 to 10. In such embodiments, a legend may be provided to inform the user of the direction of the scale (e.g., if 1 represents very significant or very insignificant). The rating scale 100 may be a mechanical input (such as a slider, knob, dial, or others) or a virtual input (such as a graphical slider, knob, dial, or other icon on a touch screen), and the position of the user's touch or input along the rating scale 100 may be converted to a numerical value (such as a value between 1 and 100). In certain embodiment, the rating scale 100 may be a graphical icon illustrating the range of possible significance ratings. In such embodiments, a significance rating 112 may be displayed on the display 16 and may be adjusted using one or more of the control inputs 20, such as a pair of up and down arrows, a keypad, and so forth.

Figure 4:
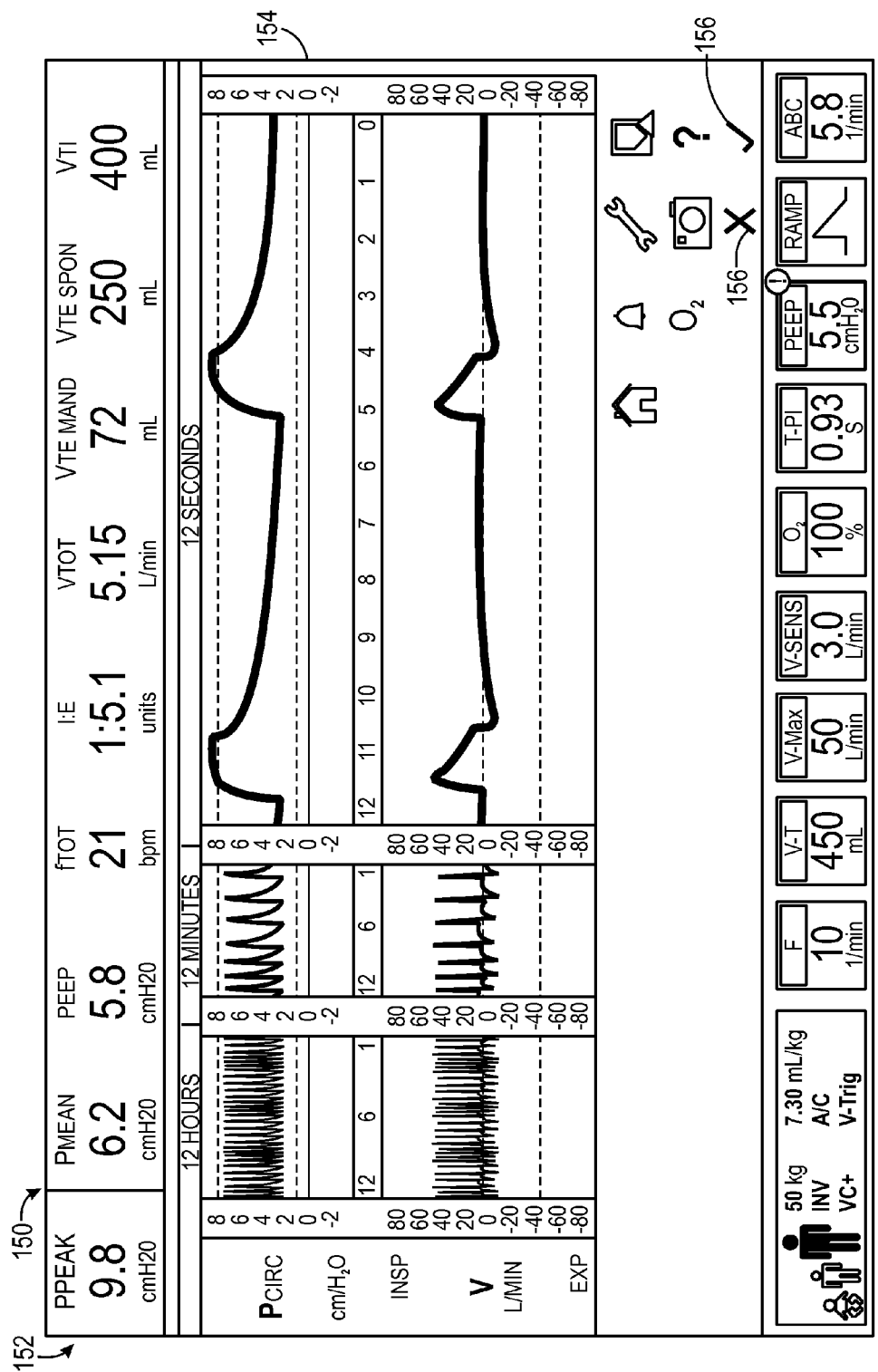
FIG. 4 is a perspective view of a ventilator with an alarm relevance input on a touch-sensitive display screen, in accordance with an embodiment.

While the embodiments described above relate to medical monitoring devices, the present techniques may also be used with therapeutic medical devices. For example, a therapeutic medical device 150 according to an embodiment is illustrated in FIG. 4. In the illustrated embodiment, the medical device 150 is a ventilator 152 configured to provide assisted breathing to a patient. In other embodiments, the medical device 150 may be any suitable type of therapeutic medical device, such as infusion pumps, dialysis machines, warming blankets, and others. The ventilator 152 may include a touch screen 154 with one or more relevance inputs 156 that are configured to generate a respective relevance indicator regarding the relevance or significance of a triggered alarm. The one or more relevance inputs 156 may be any of the inputs described herein with respect to other embodiments and figures. Further, it should be noted that the methods and techniques described herein to collect and analyze data regarding the relevance and usefulness of alarms are applicable to both medical monitoring devices and medical therapeutic devices.

Figure 5:
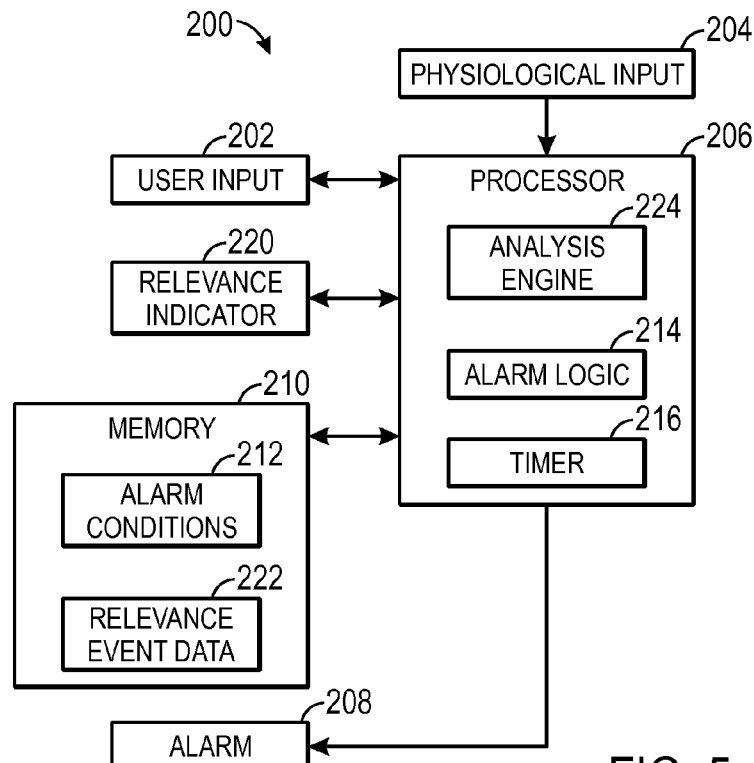
FIG. 5 is a block diagram of components of a medical system, in accordance with an embodiment.

A block diagram illustrating a processing system 200 for collecting and analyzing relevance data is illustrated in FIG. 5. The block diagram illustrates the interactions among some of the components of the system 200, including a user input 202, physiological input 204, processor 206, alarm 208, and memory 210 storing alarm conditions 212. The processor 206 may receive physiologic data from the physiological input 204. The physiological input 204 may include an incoming raw or processed physiologic signal, or measured or calculated physiologic data. The physiological input 204 may be received from a sensor coupled to the patient (e.g., the sensor 14) or from other medical devices. The processor 206 may be configured to apply alarm logic 214 that generates an alarm status based on the physiological input 204 and the stored alarm conditions 212. In response to a generated alarm status, the processor 206 may activate the alarm 208 by activating a sound, a buzzer, a vibration, a light, a text message, and/or any other suitable action.

In certain embodiments, the processor 206 may be configured to apply a time limit for receiving relevance input after an alarm is generated. For example, when an alarm status is generated, the processor 206 may activate the alarm 208 and start a timer 216. The timer 216 may include a running clock, an incrementing counter, or other suitable mechanism. The timer 216 runs until it reaches a specified limit unless a relevance rating or input is received earlier. This timer 216 may be useful to limit user input to a short duration after the alarm is triggered, such as within thirty seconds, five minutes, ten minutes, 24 hours, or any suitable time window, to increase the likelihood that the user input is accurate and not based on later faulty recollection of the events. The time limit may be user-adjustable and may be displayed as a countdown 218 (see FIG. 3, showing 29 seconds remaining) on the display of the medical device to prompt the user to enter the relevance feedback. In an embodiment, if a user does not provide feedback during the predetermined time window, the medical device may provide a separate mechanism for entering feedback at a later time, such as during a review of the patient's historical trend data. Thus, a caregiver may still provide feedback later when reviewing all of the data surrounding the alarm. However, such input may be down-weighted by the processor 206 as less likely to be accurate than input given in real-time. It should be noted that although a greater amount of time between when the alarm is triggered and when the user provides feedback might adversely the user's ability to accurately recall, a non-immediate, but short delay might actually demonstrate a more accurate or the most accurate result. For example, the clinician may provide care, if needed, for the patient before providing the feedback and/or evaluate the patient's condition before providing feedback during the short delay, whereas providing immediate feedback may represent a gut-reaction.

The relevance input is received through the user input 202. The user input 202 may take the form of one of the relevance inputs described above. When the user input 202 is activated, the processor 206 generates a relevance indicator 220. Examples of the relevance indicator 220 include a binary flag, a category indicator, an integral value, and a real numbered value. For example, a significance flag may be set to TRUE or FALSE, a category tag (Very Significant, Somewhat Significant, etc.) may be selected, or an integer value or real numbered value may be assigned. This relevance indicator 220 is stored in the memory 210 along with other applicable data such as concurrent physiological, patient, or monitor conditions. Collectively, this information regarding the alarm event may be referred to as relevance event data 222, which can be stored in the memory 210. The stored relevance event data 222 may include all or a subset of many different types of data, including the generated relevance indicator 220, time and date information, patient physiologic information, device status information, and other information about the event, facility, patient, device, or environment. Examples of this data are described in more detail next.

In certain embodiments, the stored relevance event data 222 includes information about the generated alarm 208. This data may include the type of alarm that triggered (such as a high pulse rate alarm, or low respiration rate alarm, or sensor disconnected alarm, or others), the date and time that it was triggered, the duration of time that the alarm sounded before it was silenced or canceled, the severity of the alarm, the frequency and types of other alarms over a specified time period before or after the generated alarm or the relevance input, and other data. The medical device may store two relevant timestamps. In particular, the medical device may store the time that the alarm was triggered and the time that the user provided the relevance feedback. This may be useful in assessing the time delay between the two events and determining the weight given to the user's feedback. The relevance event data 222 may also include data regarding alarms that were not rated. For example, a total number of alarms generated may be stored, including those that were not rated, so that a frequency of rated alarms can be determined.

In certain embodiments, the stored relevance event data 222 may also include physiological parameter data associated with the alarm event. For example, the medical device may store the value of the physiological parameter that violated the alarm condition and triggered the alarm. In certain embodiments, the medical device may store the value of this physiological parameter when the alarm was triggered and may also store historical data for this physiological parameter within a specified time window before and/or after the triggered alarm. Additionally, the medical device may store physiological parameter data for physiological parameters that did not trigger the alarm. This data may also be stored at the time of the alarm as well as trend data before and/or after the alarm event. For example, in certain embodiments, the medical device may store historical data for other, non-alarming physiologic parameters calculated by the medical device or calculated by other medical devices in communication (such as wired or wireless networking) with the medical device or with the analyzing processor. This may assist in evaluating the patient's condition and determining whether the triggered alarm had clinical significance or not. It also may assist in identifying correlations between various parameter values during insignificant as well as significant alarms.

Additionally, the stored relevance event data 222 may include information about the patient such as patient characteristics (e.g., age, weight, height, gender, race, condition, diagnosis, or others) or the patient's overall health index. In some embodiments, the patient health index is a numerical value provided by the user. For example, a caregiver may assess the physiological parameter data of the patient and determine a patient health index. Referring to FIG. 3, the user may enter the patient health index via one or more of the control inputs 20, and the monitor 12 may be configured to display a value of the patient health index 130 on the display 16. In some embodiments, the patient health index 130 may be a numeric value between 1 and 10, between 1 and 5, or between 1 and 3. In other embodiments, the patient health index 330 may be a numeric value between −5 and 5 or between −3 and 3, where a patient health index of 0 is indicative of an acceptable or normal physiological status and a higher patient health index (positive or negative) is indicative of a worsening physiological status.

In some embodiments, the patient health index 130 may be a modified early warning score (MEWS) that may be determined based at least in part upon the patient's systolic blood pressure, heart rate, respiratory rate, temperature, oxygen saturation, respiratory support, urine output, pain score, and/or a level of consciousness (e.g., alert, voice responsive, pain responsive, or unresponsive). In one embodiment, the processor 206 may be configured to calculate the value of MEWS using physiological parameter data calculated by the processor 206 and/or physiological parameter data received from other monitoring devices. It should be appreciated that the value of MEWS is one example of a suitable patient health index 130, and in other embodiments, the patient health index 130 may be determined using different techniques and/or algorithms.

To provide a more meaningful assessment of the health of the patient at the time of the triggered alarm, the patient health index 130 may be determined by or provided to the medical device (e.g., the monitor 12) within a predetermined time after a triggered alarm. For example, it may be desirable to enable the user to enter the patient health index 130 or to configure the medical device to determine the patient health index 130 within the predetermined time after the triggered alarm. In some embodiments, the predetermined time may between approximately thirty seconds and one hour, one minute and forty-five minutes, two minutes and thirty minutes, three minutes and fifteen minutes, or any other suitable time range. In some embodiments, the medical device may be configured to display an indicator on the display to prompt the user to provide the patient health index 130 or information (e.g., the pain score and/or the level of consciousness) to determine the patient health index 130. In some embodiments, the patient health index 130 may be determined prior to a triggered alarm. For example, the patient health index 130 may be determined when the patient is first examined by a caregiver, each time the patient is examined by the caregiver, or at any other suitable frequency. Additionally, the medical device may be configured to store a timestamp for the time when the patient health index 130 was entered or determined, which may be stored as relevance event data 222.

In some embodiments, the medical device may store relevance event data 222 for only those alarm events that are indicated as clinically insignificant, or only those that are indicated as clinically significant, for further analysis.

Additionally, in some embodiments, the processor 206 may include a statistical analysis engine or machine learning engine 224. The statistical analysis engine or machine learning engine 224 may analyze the collected relevance event data 222 to identify and modify nuisance alarm conditions. This analysis is described in more detail below with reference to FIG. 7.

Referring again to FIG. 5, the block diagram illustrates modules that represent circuit modules that may be implemented as hardware and/or software. It should be noted that the various components of the system 200 may be connected via wired or wireless connections. The components may be separate from each other, or various combinations of components may be integrated together into a medical monitor or processor, or contained within a workstation with standard computer hardware (for example, processors, circuitry, logic circuits, memory, and the like). The system 200 may include processing devices such as microprocessors, microcontrollers, integrated circuits, control units, memory (such as read-only and/or random access memory), and/or other hardware. One or more system components may be housed within a smart cable, a cable adapter, or the like. Further, one or more system components may connect to an external device such as a medical sensor, a cellular or smart phone, tablet, other handheld device, laptop computer, monitor, or the like that may be configured to receive data and show the data on a display of the device.

The systems and methods described herein may be provided in the form of tangible and non-transitory machine-readable medium or media (such as a hard disk drive, etc.) having instructions recorded thereon for execution by a processor or computer. The set of instructions may include various commands that instruct the computer or processor to perform specific operations such as the methods and processes of the various embodiments described herein. The set of instructions may be in the form of a software program or application. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other suitable storage medium.

As described above, the system 200 may be configured to store relevance indicators 220 and relevance event data 222. Additionally, the system 200 may be configured to analyze the relevance indicators 220 and the relevance event data 222 to identify nuisance alarms and modify alarm conditions to reduce nuisance alarms. The present embodiments also provide various methods for storing and analyzing the relevance indicators 220 and the relevance event data 222. For example, as will be described below with reference to FIGS. 6 and 7, methods for collecting and storing relevance indicators and relevance event data are provided. Additionally, as will be described below with reference to FIGS. 8 and 9, methods for analyzing stored relevance indicators and relevance event data are provided.

Figure 6:
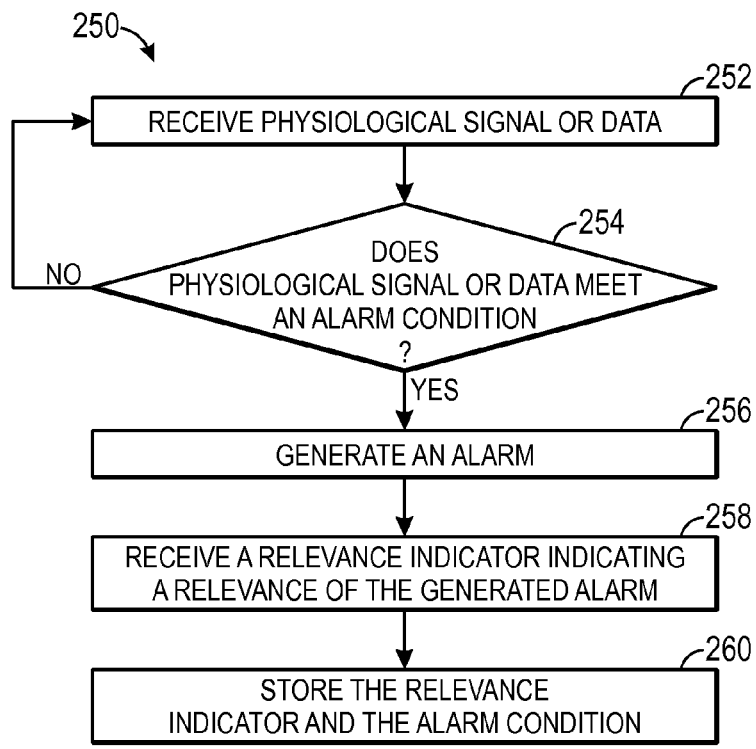
FIG. 6 illustrates a flow diagram of a method for gathering relevance event data, in accordance with an embodiment.

FIG. 6 illustrates a method 250 for collecting relevance data for triggered alarms in accordance with an embodiment. The method 250 includes receiving a physiological signal or physiologic data (block 252). For example, the physiological signal or physiologic data may be received from a sensor (e.g., the sensor 14) or from one or more local or remote medical devices. In some embodiments, the method 250 may include receiving a plurality of physiological signals or a plurality of physiological parameter values. Further, in some embodiments, the plurality of physiological signals may include at least two different types of physiological signals (e.g., a photoplethysmograph signal, an electrocardiography signal, a blood pressure signal, etc.) and the plurality of physiological parameter values may include at least two different types of physiological parameter values (e.g., oxygen saturation, heart rate, respiration rate, blood pressure, BISPECTRAL™ index, etc.). The method 250 also includes determining whether the physiological signal or physiologic data meets an alarm condition (block 254). If the alarm condition is not met, the method 250 may continue to receive the physiological signal or physiologic data (block 252). In response to determining that the physiological signal or physiologic data meets the alarm condition, the method 250 includes generating an alarm (block 256). Additionally, the method 250 includes receiving a relevance indicator (e.g., the relevance indicator 220) indicating the relevance of the generated alarm (block 258) and storing the relevance indicator and the alarm condition (block 260).

Figure 7:
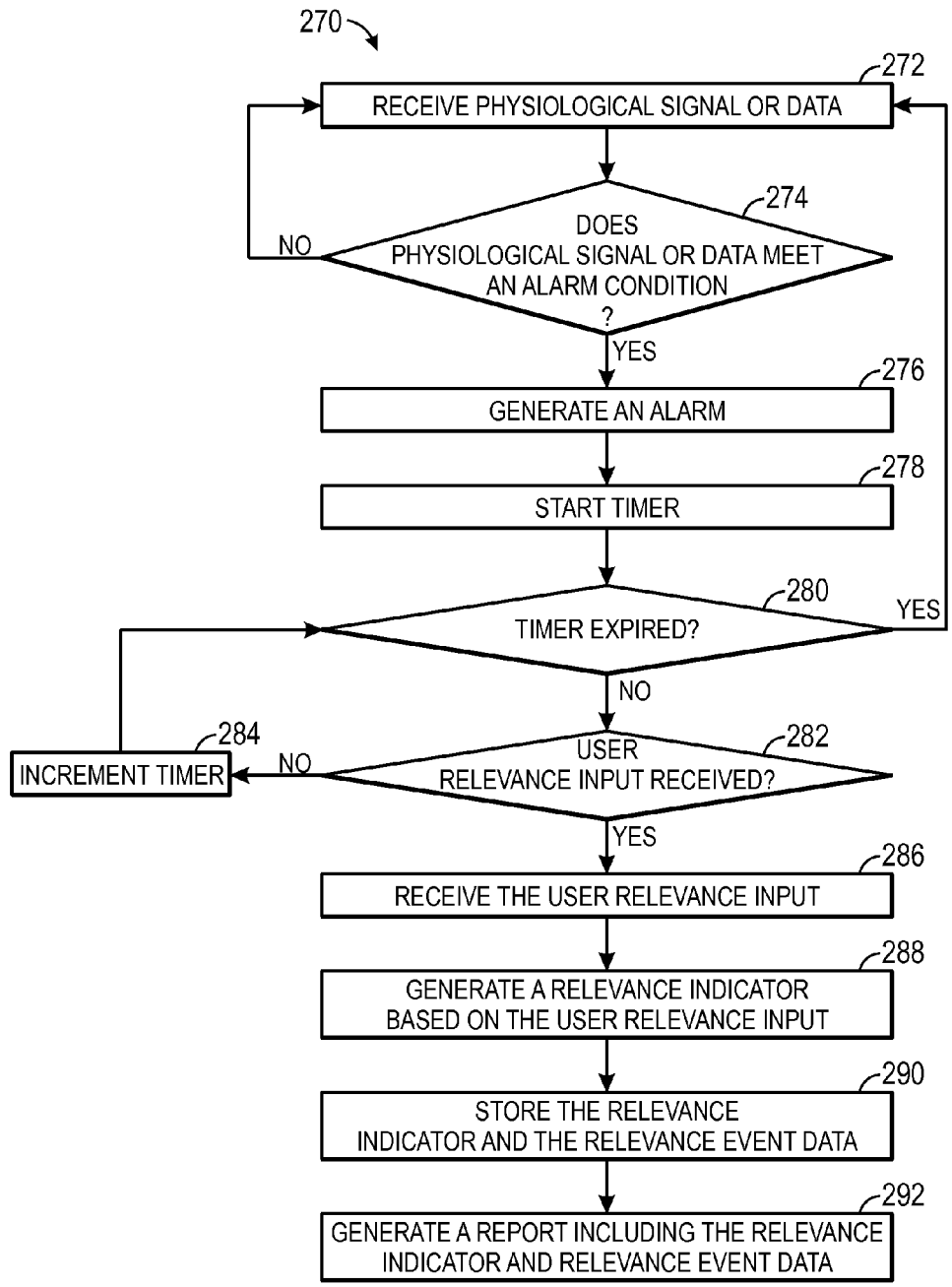
FIG. 7 illustrates a flow diagram of a method for gathering relevance event data, in accordance with an embodiment.

Additionally, FIG. 7 illustrates a method 270 for collecting relevance indicators and relevance event data for triggered alarms in accordance with an embodiment. The method 270 includes receiving a physiological signal or physiologic data (block 272) and determining whether an alarm condition is met (block 274). If the alarm condition is not met, the method 270 may continue to receive the physiological signal or physiologic data (block 272). In response to determining that the physiological signal or physiologic data meets the alarm condition, the method 270 includes generating an alarm (block 276). In certain embodiments, the method 270 may also include starting a timer (block 278) when the alarm is generated. The timer may expire after a preset time. The method 270 may include determining whether the timer has expired (block 280). If the timer has expired without any relevance data being received, the method 270 may return to block 272. If the timer has not expired, the method 270 includes determining whether a user relevance input has been received (block 282). If a user relevance input has not been received, the method 270 includes incrementing a timer (block 284) and continues to determine whether the timer has expired (block 280). In response to determining that a user relevance input was received, the method 270 includes receiving the user relevance input (block 286), generating a relevance indicator (e.g., the relevance indicator 220) based on the user relevance input (block 288), and storing the relevance indicator and relevance event data (e.g., relevance event data 222) (block 290).

Further, the method 270 may include generating a report including the relevance indicator and the relevance event data (block 292). The report may be displayed on a display of the medical device or on a display of another suitable processing device. In certain embodiments, the report may be generated after a predetermined number of relevance indicators (and associated relevance event data) are stored. For example, the report may be generated after 1 to 5000 relevance indicators are stored, 5 to 1000 relevance indicators are stored, 10 to 500 relevance indicators are stored, or any other suitable number of relevance indicators is stored. The report may be generated by the medical device that generated the alarm and stored the relevance indicators and relevance event data, or may be generated by another processing device that is configured to receive the relevance indicators and relevance event data from the medical device. The report may be provided to the user in any suitable format, such as a list, a chart, a bar graph, a pie chart, and so forth.

In certain embodiments, the report may include a histogram illustrating the distribution of the number of relevance responses for a particular alarm or alarm condition. The histogram may be generated using binary relevance feedback (e.g., relevant or irrelevant, or 0 or 1) and/or rating scale feedback (e.g., a rating between 1 and 5). In certain embodiments, the histogram may be scaled. For example, if the user wanted to rate the relevance responses with a rating of 5 (e.g., very significant), the number of relevance response with the rating of 5 may be scaled up on the histogram by a predetermined number or a predetermined percentage. In some embodiments, a plurality of histograms may be generated for a plurality of alarm conditions. The alarm conditions for the histograms may be user-selected or may be selected by the medical device based on the relevance event data. Additionally, in some embodiments, the plurality of histograms may include different levels of alarm conditions. For example, a first histogram may include the distribution of relevance responses for all types of pulse oximetry alarms (e.g., for a predetermined number of alarm events with one or more medical devices and one or more patients), second histogram may include the distribution of relevance responses for pulse oximetry alarms with a particular alarm condition (e.g., a predetermined threshold for minimum oxygen saturation), a third histogram may include the distribution of relevance responses for pulse oximetry alarms when the patient's heart rate is in a normal range, and so forth.

Providing the different histograms may facilitate the identification of nuisance alarms and patterns between alarm conditions and nuisance alarms. For example, the skewness of the histogram may be determined to evaluate whether the alarm condition of the histogram is predominantly relevant or irrelevant. In certain embodiments, the medical device or another processing device may assign a numerical relevance score (e.g., 0 for irrelevant and 1 for relevant) to the histogram based on the skewness.

It should be noted that while FIG. 7 does not include the flow of steps that may be taken to acknowledge, silence, cancel, or otherwise respond to the generated alarm, or steps that may be taken to prompt the user to enter any additional information (such as the patient's health index at the time of the alarm), these additional steps may be included in some embodiments. It should also be noted that the physiologic signal or data is continually received at block 252 of FIG. 6 and block 272 of FIG. 7, initiating a new instance of the method with each incoming data point or data segment.

Figure 8:
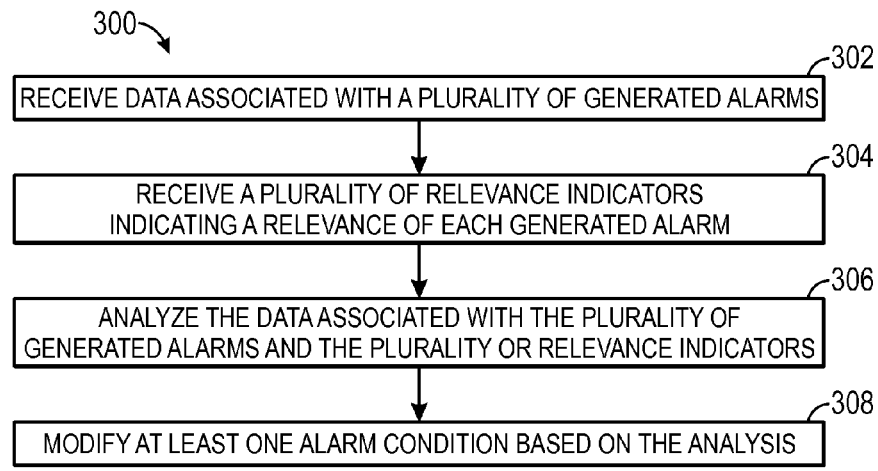
FIG. 8 illustrates a flow diagram of a method for modifying alarm conditions to reduce nuisance alarms, in accordance with an embodiment.

FIG. 8 illustrates a method 300 for analyzing relevance data and modifying alarm conditions to reduce nuisance alarms. The method 300 includes receiving data associated with a plurality of generated alarms (block 302). In particular, each generated alarm may be generated in response to a determination that a respective physiological parameter of one or more patients meets a respective alarm condition. The generated alarms may be generated by one or more medical devices (e.g., medical monitoring devices or medical therapeutic devices) in use with one or more patients. The data associated with the plurality of generated alarms may include the alarm conditions and other relevance event data, as described in detail above.

The method 300 also includes receiving a plurality of relevance indicators indicating a relevance of each of the plurality of generated alarms (block 304). In some embodiments, the data associated with the plurality of generated alarms and the relevance indicators may be received by a medical device (e.g., a medical device in use with a patient) or by another processing device configured to receive data from one or more medical devices configured to store the relevance indicators and the relevance event data.

Further, the method 300 includes analyzing the data associated with the plurality of generated alarms and the plurality of relevance indicators (block 306). The data may be analyzed by the collecting device or may be transmitted from the collecting device to another processing device for analysis. The processing device may analyze data from many different medical devices, patients, and/or care facilities.

Analyzing the data and the relevance indicators may include performing statistical analysis on the collected data. Statistical analysis procedures may include principal component analysis (PCA), matrix techniques, independent component analysis (ICA), linear regression, linear combination, multivariate analysis, linear discriminate analysis (LDA), statistical analysis methods; neural networks (e.g., multilayer perception networks (MLP) or radial basis networks), stochastic or probabilistic classifiers (e.g., Bayesian, Hidden Markov Model (HMM), or fuzzy logic classifiers), genetic-based algorithms, propositional or predicate logics (e.g., non-monotonic or modal logics), nearest neighbor classification methods (e.g., kth nearest neighbor or learning vector quantization (LVQ) methods), or any other classification or learning-based algorithms.

Analyzing the collected data may include identifying nuisance alarm conditions. For example, identifying nuisance alarm conditions may include identifying an alarm condition that has a low relevance value, such as a relevance value below a threshold, or a high irrelevance value, such as an irrelevance value above a threshold. Identifying nuisance alarms may also include identifying patterns of data with low relevance values or high irrelevance values, such as combinations of physiological parameter conditions and alarm conditions. Identifying nuisance alarms may also include identifying a correlation between relevance values and the patient's condition, such as low relevance values associated with alarms that occur when the patient's oxygen saturation is above 90%. The data analysis that identifies low-relevance alarms may take place after a threshold number of user feedback inputs have been received.

Additionally, the method 300 may include modifying at least one of the alarm conditions based on the analysis (block 308). In particular, the at least one alarm condition may be modified to reduce nuisance alarms and to improve the relevancy of the generated alarms. Modifying the alarm conditions may include changing an alarm threshold, such as moving it up or down, to reduce the number of alarm events. For example, an alarm condition may include a lower threshold of 90% for oxygen saturation, and modifying this alarm condition may include reducing the threshold to 89% or 85% or other appropriate value.

In another embodiment, analysis of the collected relevance event data may reveal a relationship between two or more physiologic parameters, and modifying the alarm condition may include combining alarm conditions from two or more physiologic parameters. The new combined alarm is not triggered unless both (or all) conditions are met. For example, an initial alarm condition may trigger an alarm when oxygen saturation falls below 90%. Data analysis may show that oxygen saturation between 85% and 90% is not clinically significant while the patient's respiration rate remains above 11 beats per minute (bpm), and may show that a drop in oxygen saturation below 90% is clinically significant at times when the patient's respiration rate is below 11 bpm. Accordingly, a modified alarm condition may trigger an alarm when oxygen saturation is below 90% and respiration rate is below 11 bpm. As another example, the processing device may determine that an oxygen saturation value below 90% while respiration rate is below 11 bpm is not clinically significant unless the patient's systolic blood pressure is less than 40 mmHg, the patient's heart rate is less than 30 bmp, or the patient's health index is below a threshold. Accordingly, a new alarm protocol may be created that triggers an alarm when these identified conditions are all met at the same time. As another example, the processing device may determine that an oxygen saturation value below 90% is not clinically significant when the patient's health index is between −1 and 1. Accordingly, a new alarm protocol may be created that reduces the 90% threshold, or reduces the severity of the alarm. The new alarm protocol is based on data showing the relevance of alarms with those characteristics, and thus the new or modified alarm protocol is likely to reduce nuisance alarms.

As another example, combining alarm conditions from two or more physiologic parameters may include creating one combined threshold value, rather than monitoring each parameter with respect to its own threshold. When a number N of different parameters are being monitored together, the problem may be viewed as a position in N-dimensional space, with the center representing a healthy patient. As one or more parameters diverge from healthy values, the patient's position in N-dimensional space moves away from the center. An alarm threshold may be established based on a distance from the center, and an alarm may be triggered when this distance is reached. This distance may not be the same in all directions, depending on the relationship between the parameters. These relationships may be stored in the form of a covariance matrix. The N physiological parameters that are combined into this alarm may be combined in a weighted average, with some parameters weighted more heavily than others, and with weights varying based on the status of other parameters.

In an embodiment, modifying alarm conditions may include modifying a threshold or other condition to be a function of another physiologic parameter. For example, an alarm threshold for oxygen saturation may vary with respiration rate. In one example, when the patient's respiration rate is above a threshold, such as 11 bpm, the oxygen saturation threshold is lowered, and when the respiration rate falls below a threshold, the oxygen saturation threshold is increased. These may be stepwise changes or continuous changes in threshold based on the value of the other parameter. Thresholds or other alarm conditions may also vary with patient characteristics such as age, weight, gender, or others. Alarm conditions that rely on multiple parameters may be enabled or disabled based on the available parameters in a particular situation with a particular patient.

Further, in certain embodiments, modifying alarm conditions may include tagging an alarm with a nuisance or low-value identifier, to identify it as a potential nuisance alarm. This identifier can be used to create a display on the screen to advise the caregiver that the alarm is potentially of low relevance. In another embodiment, modifying alarm conditions may include reducing the severity of the alarm when the alarm condition shows consistently low relevance values.

Figure 9:
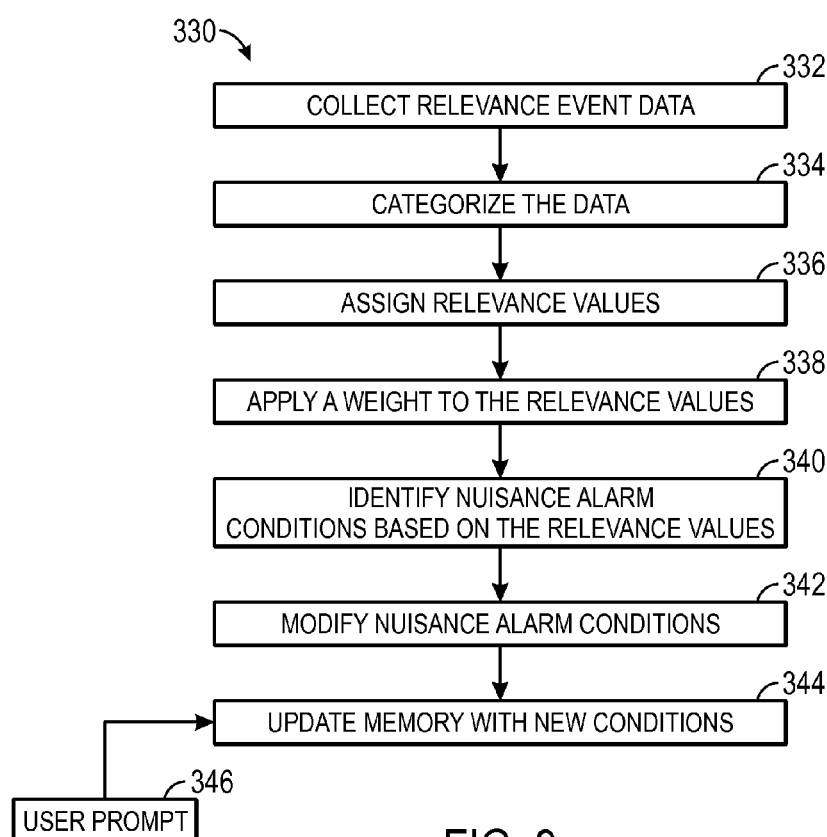
FIG. 9 illustrates a flow diagram of a method for modifying alarm conditions to reduce nuisance alarms, in accordance with an embodiment.

FIG. 9 illustrates an embodiment of a method 330 for analyzing relevance data and modifying alarm conditions to reduce nuisance alarms. The method 330 includes collecting relevance event data (bock 332). The data may be collected over a period of time such as a few hours of data from a single patient, multiple days of data from a single patient, hours of data from multiple patients, or much more data collected across many patients. The types of data collected have been described above.

The method 330 also includes categorizing the collected data (block 334). This may include organizing the data into categories that will be analyzed together. Categories may include the physiologic parameter that alarmed, the alarm severity, the medical facility, the patient's characteristics, or other helpful categories. For example, collected relevance event data may be sorted into groups of data associated with oxygen saturation alarms, data associated with heart rate alarms, data associated with capnography alarms, data associated with respiration rate alarms, and so on. As another example, the collected data may be sorted into groups of data associated with different medical facilities (such as hospitals, nursing homes, skilled nursing centers, outpatient centers, urgent care facilities, doctor offices, and others), so that each facility may optimize their alarm protocols according to their own best practices. As another example, the collected data may be sorted based on the time delay between the alarm and the user's input, in order to assess trends in the relevance rating as a function of delay time. As another example, the collected data may be sorted based on the particular alarm condition that was triggered, such a low heart rate alarm, a high blood pressure alarm, a pulse oximetry sensor disconnect alarm, and so on.

The method 330 further includes assigning a relevance value (e.g., a relevance indicator) to each rated alarm event (block 336). The relevance value may be based on the relevance feedback provided by the user. When the user input is binary (e.g., relevant or not relevant), this may include assigning a value of 1 for "relevant" and 0 for "not relevant" inputs. When the user provides a rating on scale, assigning a value may include assigning a numerical value to the user's input (such as a 5 for highly relevant, a 4 for somewhat relevant, and so on to 0 for highly irrelevant), using the numerical value that the user provided (e.g., if the user inputs a number between 0 and 5), or converting the user's graphical input into a number (such as the location of a user's input along a scale).

In certain embodiments, the relevance value includes two values (i.e., a relevance value and an irrelevance value). For example, when the user inputs "highly relevant", the processor may store a relevance value of 3 and an irrelevance value of 0. When the user inputs "somewhat relevant", the processor may store a relevant value of 1 and an irrelevance value of 0. When the user inputs "somewhat irrelevant", the processor may store a relevance value of 0 and an irrelevance value of 1. Further, when the user inputs "highly irrelevant", the processor may store a relevance value of 0 and an irrelevance value of 3. It should be noted that the numerical values assigned from a Likert-type scale or graphical scale need not be linear; more extreme inputs, such as highly relevant or highly irrelevant, may be increased disproportionately. By providing two relevance values for each triggered alarm, relevance and irrelevance can be separately numerically tracked. It should be understood that these values may be assigned based on other types of user inputs described herein, such as binary inputs, graphical inputs, and numerical inputs.

In some embodiments, the method 330 may include applying a weight to the relevance values (block 338). For example, a weight may be a number between 0 and 2, which is applied as a multiplier to the relevance value or the irrelevance value, to adjust these values based on additional circumstances. A weight may be chosen based on several different factors. In an embodiment, one factor is the extremity of the user input. For example, significance ratings that are more extreme (such as strongly disagree, strongly agree, very significant, very insignificant, or numeric values at the ends of the rating scale) are weighted more heavily than more neutral ratings. That is, the weight applied to these relevance values is increased, to weight them more heavily in the analysis. This increased weight is based on the assumption that a more extreme input is more likely to be accurate than a neutral input, which may reflect poor recollection from the user. For example, when a user inputs an integer number between 0 and 5 to indicate the relevance of the alarm, with increasing number meaning increasing relevance, an increased weight may be applied to an entry of 0 or 5. For example, when a user enters "0", the processor may store a relevance value of 0 and an irrelevance value of 5. At step 338, an increased weight (for example, 1.5 or 2) may be applied to the irrelevance value due to the extremity of the input. The weighted irrelevance value is then stored as 7.5 or 10. Similarly, if the user enters "5", the processor may store a relevance value of 5 and an irrelevance value of 0, and an increased weight (for example, 1.5 or 2) may be applied to the relevance value, leading to a weighted value of 7.5 or 10.

In another embodiment, the medical device may reduce the weight of a relevance value or an irrelevance value that was received after a threshold delay from the time the alarm was triggered. This down-weighting is based on the assumption that the user's response is less likely to be accurate the more delayed it is from the alarm event. In another embodiment, user inputs that are provided too fast (e.g., within a very short time duration from the alarm event) may also be down-weighted as too hasty. In an embodiment, relevance input from the user is given a weight, and the weight is initially increased and then reduced as a function of the delay between the alarm event and the relevance input. Weights may be changed in a step-wise or continuous manner.

The method 330 also includes identifying nuisance alarms based on the relevance values (block 340). As described in detail above, identifying the nuisance alarms may include identifying an alarm condition that has a low relevance value, identifying an alarm condition that has a high irrelevance value, or identifying patterns of data with low relevance values or high irrelevance values. Further, as noted above, identifying the nuisance alarms may include statistic analysis of the relevance event data and relevance values.

Additionally, the method 300 includes modifying alarm conditions to reduce nuisance alarms (block 342). Modifying the alarm conditions may include the techniques described above with respect to FIG. 8. Additionally, the method 300 may include updating a memory of a medical device based on the modified alarm conditions (block 344). For example, in some embodiments, the medical device may be a learning device (e.g., a smart device) that adaptively modifies alarm conditions to reduce nuisance alarms and continuously updates an algorithm stored in a memory to implement the modified alarm conditions. Such an algorithm may iterate on its own modified protocols to continue to improve the protocols to reduce nuisance alarms. In other embodiments, updating the memory may require an input from the user (block 3460c) to confirm that the new or modified alarm conditions should be implemented. Additionally, in some embodiments, updating the memory may include removing alarm protocols or conditions associated from the medical device (such as from the stored alarm conditions 212 in memory 210 in FIG. 5). This may be done for alarm conditions that return a very low relevance value after a sufficient amount of user feedback.

It should be understood that embodiments described herein are exemplary in nature, and examples given are intended to be explanatory and not limiting.

What is claimed is:

1. A method, comprising:
receiving a physiological signal or a physiological parameter value;
generating an alarm in response to a determination that the physiological signal or physiological parameter value meets an alarm condition;
receiving a relevance indicator indicating a relevance of the generated alarm;
storing the relevance indicator and the alarm condition;
repeating the steps of receiving the physiological signal, generating the alarm, receiving the relevance indicator, and storing the relevance indicator to store a plurality of relevance indicators and a plurality of corresponding alarm conditions;
analyzing the plurality of relevance indicators and the plurality of corresponding alarm conditions; and
modifying at least one alarm condition of the plurality of corresponding alarm conditions based on the analyzing.

2. The method of claim 1, wherein the alarm condition comprises a physiologic threshold or range.

3. The method of claim 1, comprising assigning a relevance value or an irrelevance value to the generated alarm based on the received relevance indicator.

4. The method of claim 1, comprising storing physiologic data corresponding in time to the generated alarm.

5. The method of claim 1, wherein repeating the steps of claim 1 a predetermined number of times comprises receiving at least two different types of physiological signals or at least two different types of physiological parameter values.

6. The method of claim 1, comprising generating a histogram illustrating a distribution of relevance indicators associated with an alarm condition of the plurality of corresponding alarm conditions.

7. A method, comprising:
receiving data associated with a plurality of generated alarms, wherein each of the plurality of generated alarms is generated in response to a determination that a respective physiological parameter of a patient meets a respective alarm condition;
receiving a plurality of relevance indicators indicating a relevance of each of the plurality of generated alarms;
analyzing the data associated with the plurality of generated alarms and the plurality of relevance indicators; and
modifying at least one alarm condition of the alarm conditions based on the analysis.

8. The method of claim 7, comprising assigning a relevance value or an irrelevance value to each of the plurality of generated alarms based on respective relevance indicator.

9. The method of claim 8, comprising identifying a nuisance alarm condition having a relevance value below a predetermined minimum threshold or having an irrelevance value above a predetermined maximum threshold.

10. The method of claim 9, comprising modifying the nuisance alarm condition to increase the relevance value or to decrease the irrelevance value.

11. The method of claim 10, wherein modifying the nuisance alarm condition comprises changing a threshold value or changing a severity of the nuisance alarm condition.

12. The method of claim 10, wherein modifying the nuisance alarm condition comprises changing a threshold value as a function of a physiological parameter value.

13. The method of claim 7, comprising generating a histogram illustrating a distribution of relevance indicators associated with an alarm condition of the alarm conditions.

14. A medical device, comprising:
- a signal input configured to receive a physiologic parameter value;
- a processor configured to activate an alarm in response to a determination that the physiologic parameter value meets an alarm condition;
- a user input configured to generate a relevance indicator indicating a relevance of the alarm; and
- a memory configured to store a plurality of relevance indicators and a plurality of corresponding alarm conditions over time,
    - wherein the processor is configured to analyze the plurality of relevance indicators and the corresponding plurality of alarm conditions, and
    - wherein the processor is configured to modify at least one alarm condition of the plurality of alarm conditions based on the analysis.

15. The medical device of claim 14, wherein the user input comprises a mechanical button on the medical device.

16. The medical device of claim 14, comprising a touch-sensitive display, and wherein the user input comprises a selectable graphic displayed on the touch-sensitive display.

17. The medical device of claim 14, wherein the user input comprises first and second user inputs generating first and second relevance indicators, respectively, and wherein the first relevance indicator comprises an indication of a high relevance, and wherein the second relevance indicator comprises an indication of a low relevance.

18. The medical device of claim 14, wherein the user input comprises a numeric scale and the relevance indicator comprises a rating on the numeric scale.

19. The medical device of claim 14, wherein the processor is configured to assign a relevance value based on the relevance indicator and to identify a nuisance alarm condition in response to a determination that the relevance value is below a predetermined threshold.

20. The medical device of claim 19, wherein the processor is configured to modify the nuisance alarm condition to increase the relevance value.

* * * * *